United States Patent [19]

Bertoni et al.

[11] Patent Number: 5,858,672
[45] Date of Patent: Jan. 12, 1999

[54] NUCLEIC ACID FRAGMENTS AND CORRESPONDING PEPTIDE FRAGMENTS FROM THE CAPRINE ARTHRITIS-ENCEPHALITIS VIRUS (CAEV) GENOME, AND USES THEREOF

[75] Inventors: Giuseppe Bertoni, Uberstorf, Switzerland; Gianfranco Pancino, Paris, France; Ernst Peterhans, Berne, Switzerland; Pierre Sonigo, Paris, France

[73] Assignee: Centre National de la Recherche Scientifique, Paris Cedex, France

[21] Appl. No.: 750,856

[22] PCT Filed: Jun. 26, 1995

[86] PCT No.: PCT/FR95/00848

§ 371 Date: Apr. 8, 1997

§ 102(e) Date: Apr. 8, 1997

[87] PCT Pub. No.: WO96/00784

PCT Pub. Date: Jan. 11, 1996

[30] Foreign Application Priority Data

Jun. 28, 1994 [FR] France .................... 94 07933

[51] Int. Cl.$^6$ .............. C12Q 1/08; G01N 33/53; C07J 14/155; C07J 16/10
[52] U.S. Cl. .............. 435/6; 435/7.1; 435/91.2; 530/350; 530/389.4; 536/23.72
[58] Field of Search ................ 435/6, 7.1, 91.2; 424/159.1, 187.1; 536/23.72; 530/350, 389.4

[56] References Cited

PUBLICATIONS

Lichtensteiger et al. Virology, vol. 185, No. 1, Nov. 1991, pp. 2–9.
McGuire et al. Journal of Virology, vol. 66, No. 5, May 1992, pp. 3247–3250.
Knowles et al. Journal of Virology, vol. 65, No. 11, Nov. 1991, pp. 5744–5750.
Bertoni et al. Journal of Virology, vol. 68, No. 11, Nov. 1994, pp. 7139–7147.

*Primary Examiner*—George C. Elliott, Ph.D.
*Assistant Examiner*—John S. Brusca
*Attorney, Agent, or Firm*—Oblon, Spivak, McClelland, Maier & Neustadt, P.C.

[57] ABSTRACT

Nucleotide fragments from caprine arthritis-encephalitis virus (CAEV) env gene, corresponding peptide fragments, and uses thereof in screening for viral caprine arthritis-encephalitis, are disclosed. Antibodies to peptide fragments and uses thereof for diagnosing viral arthritis-encephalitis are also enclosed. Said nucleic acid fragments code for a peptide fragment including at least one CAEV Env protein segment comprising at least one immunodominant epitope selected from the transmembrane region of said protein, and include 15–255 nucleotides.

15 Claims, 4 Drawing Sheets

FIG. 1

```
             671                                                                        730
CAEV-CO   ----------  ----------  ----------  --------t  --|-------  ----hq----
CAEV-63   ----------  a---------  ----------  --------t  --|-------  ----hq----
OMVV-SA   ---------n  ----------  ----------  ---------  ------h---  ----------
VIS-SON   ----------  ----s-----  ----------  --------|-  -*--v-----  ----------
MVV-EV1   ---------n  ----------  ----------  ------v|-  ----v-----  ----------
CONSENSUS LANATAAQQD  VLEATYAMVQ  HVAKGVRILE  ARVARVEAIV DRMMLYQELD  CWHYQHYCVT
                          TM1                              TM2          TM3

731                                                   772
CAEV-CO   --kt------  ----------  -----rglqg  y-t--ti--k  -s
CAEV-63   ---a------  ----------  -----r-lqg  y-g--t----  -s
OMVV-SA   ---t---q--  ----------  ----------  --a-----k   --
VIS-SON   ---s---n--  ----------  ----------  --g-------  --
MVV-EV1   --ks------  ----r-----  ----------  --a---q---  --
CONSENSUS STR-EVAKYV  NWTRFKDNCT  WQQWEEEIEQ  HE-NLSLLLR  EA
                                      TM4
```

NUCLEIC ACID FRAGMENTS AND CORRESPONDING PEPTIDE FRAGMENTS FROM THE CAPRINE ARTHRITIS-ENCEPHALITIS VIRUS (CAEV) GENOME, AND USES THEREOF

This application is the National Stage of International Application No. PCT/FR95/00848 filed on Jun. 26, 1995.

BACKGROUND OF THE INVENTION

1. Field of the Invention

The present invention relates to nucleotide fragments derived from the env gene of the caprine arthritis-encephalitis virus (CAEV) and to the corresponding peptide fragments and to their applications in the screening for caprine viral encephalitis and arthritis; the present invention also relates to anti-peptide fragment antibodies as well as to their applications in the diagnosis of viral encephalitis and arthritis.

2. Description of the Related Art

The caprine arthritis-encephalitis virus is a lentivirus which causes a leukoencephalitis in young goats and a chronic clinical arthritis in 20 to 30% of adult goats infected naturally. Arthritis is usually progressive and is particularly severe at the level of the synovial spaces of the carpal joints.

The nucleotide sequence of the CAEV-CO strain has been sequenced and described (M. SALTARELLI et al., Virol., 1990, 179, 347–364), using infectious clones obtained from HindIII fragments, transfected into goat synovial membrane cells. The genome comprises 9189 nucleotides and includes successively the sequence encoding LTR, the sequences encoding the different viral proteins: Gag protein, Pol protein, the regulatory protein Q, the Tat protein, the envelope proteins and the Rev proteins.

The organization of the env gene encoding the CAEV envelope glycoprotein is similar to that of the sheep viruses (VISNA virus) and comprises a sequence encoding a surface (SU) protein and a sequence encoding a transmembrane (TM) protein which form the envelope glycoprotein.

The CAEV envelope proteins are considered to be at the centre of the host-virus relationship; their study is therefore essential for understanding the interaction of the virus with the immune system (neutralizing epitopes, B and T epitopes) and with the target cells in the infection and for developing effective diagnostic reagents.

The seriousness of the disease in the infected animals is directly correlated with the level of anti-viral envelope (Env) protein antibody, and in particular with the level of anti-transmembrane (TM) protein antibody and/or with the level of anti-surface (SU) protein antibody of the said Env envelope protein (T. C. McGUIRE et al. J. Virol., 1992, H, 5, 3247–3250; D. P. KNOWLES et al., 1991, J. Virol., 1991, 65, 11, 5744–5750).

Indeed, the immune response to the viral antigen plays an important role in the inflammation of the joints (in particular, the inflammation of the synovial spaces of the carpal joints), especially because of a massive infiltration of the said joints by lymphocytes, plasmocytes and macrophages and by an accumulation of antibodies directed against the Env protein.

In particular, the serum having a high titer with respect to monomeric (38 kDa) and oligomeric TM glycoproteins are found in goats with progressive arthritis (D. P. KNOWLES et al., J. Virol., 1990, 64, 2396–2398).

Moreover, goats vaccinated with the inactivated caprine arthritis-encephalitis virus develop a more severe arthritis, after infection in the laboratory than the control animals (McGUIRE et al., J. Vet. Res., 1986, 47, 537–540).

It is therefore vital to establish a constant supervision of the herds in order to avoid propagation of the disease, in particular by excluding the diseased animals as rapidly as possible.

At present, CAEV arthritis is essentially diagnosed by means of serological tests based on a whole virus preparation; such tests have the disadvantage of being difficult to prepare and of being expensive; they also require a particularly delicate development (problem of standardization) and can, in addition, cause false-negative reactions and/or false-positive reactions.

Other tests (ELISA tests) also exist which use recombinant Gag proteins; such tests also have the disadvantage of causing false-negative and/or false-positive reactions and create, in addition, problems of background noise.

Now, in overview, it is absolutely vital to have a reliable and inexpensive test so as to be able to test the herds as a whole in order to avoid a massive infection (especially by milk) (programme of eradication).

SUMMARY OF THE INVENTION

The present invention therefore set itself the aim of providing reagents capable of detecting arthritis caused by CAEV, which are more suitable for the requirements of practical usage, especially by allowing the development of highly specific diagnostic tests (absence of false-positive and false-negative reactions) carrying, in addition, no risk for the user and allowing rapid screening for the herds as a whole.

The subject of the present invention is nucleic acid fragments, characterized in that they encode a peptide fragment including at least one segment of the CAEV Env protein comprising at least one immuno-dominant epitope, selected from the transmembrane region of the said protein, which nucleic acid fragments comprise between 15 and 255 nucleotides.

Among these nucleic acid fragments there may be mentioned:

a fragment corresponding to positions 8003–8163 of the gene encoding the CAEV Env protein, of sequence
TAAGGCAGCTGTCCAGACCCTTGCTAAT-GCAACTGCTGCACAGCAGGATGTGTTA GAG-GCAACCTATGCCATGGTACAGCATGTG-GCTAAAGGCGTACGAATCTTGGAAG CTCGAGTGGCTCGAGTGGAAGCTATCA-CAGATAGAATAATGCTATACCAAG (SEQ ID No. 1), and encoding a peptide fragment called G1;

a fragment corresponding to positions 8019–8264 of the gene encoding the CAEV Env protein, and encoding a peptide fragment called G2;

a fragment corresponding to positions 7991–8107 of the gene encoding the CAEV Env protein and encoding a peptide fragment called G3;

a fragment corresponding to positions 8204–8360 of the gene encoding the CAEV Env protein of sequence
TACAAAAACAGAAGTAGCAAAATATAT-CAATTGGACGAGGTTTAAGGATAATTGC ACATG-GCAGCAGTGGGAGAGAGGATTACAGGGG-TATGATACAAACTTAACATTAC TGTTAAAGGAATCAGCAGCAATGACA-CAACTAGCAGAAGAGCAAGCA (SEQ ID No. 2), and encoding a peptide fragment called G4;

a fragment corresponding to positions 8090–8259 of the gene encoding the CAEV Env protein of sequence TAAAGGCGTACGAATCTTGGAAGCTC-
GAGTGGCTCGAGTGGAAGCTATCACAGAT
AGAATAATGCTATACCAAGAATTGGAT-
TGTTGGCACTATCATCAATACTGTATAA CCTCTA-
CAAAAACAGAAGTAGCAAAATATAT-
CAATTGGACGAGGTTTAAGGATAA TTGCA (SEQ
ID No, 3), and encoding a peptide fragment called G5;

a fragment corresponding to positions 8049–8093 of the gene encoding the CAEV Env protein of sequence GATGTGTTAGAGGCAACCTATGCCATGG-TACAGCATGTGGCTAAA (SEQ ID No. 4), and encoding a peptide fragment called TM1;

a fragment corresponding to positions 8130–8165 of the gene encoding the CAEV Env protein of sequence GAAGCTATCACAGATAGAATAATGC-TATACCAAGAA (SEQ ID No. 5), and encoding a peptide fragment called TM2;

a fragment corresponding to positions 8160–8204 of the gene encoding the CAEV Env protein of sequence CAAGAATTGGATTGTTGGCACTATCAT-CAATACTGTATAACCTCT (SEQ ID No. 6), and encoding a peptide fragment called TM3; and a fragment corresponding to positions 8256–8297 of the gene encoding the CAEV Env protein of sequence TGCACATGGCAGCAGTGGGAGAGAGGAT-TACAGGGGTATGAT (SEQ ID No. 7), and encoding a peptide fragment called TM4.

The subject of the present invention is also a peptide fragment, characterized in that it includes at least one segment of the CAEV Env protein, selected from the transmembrane region of the said protein, comprising between 5 and 85 amino acids and at least one immunodominant epitope, and in that it is recognized by at least 60 of the antibodies produced during an infection and/or during an inoculation by a CAEV strain.

Epitope is understood to mean, for the purposes of the present invention, the group-specific epitopes, that is to say the epitopes common to all the CAEV strains (conserved regions) and which are recognized by the antibodies directed against all the CAEV strains (group recognition).

Among these peptide fragments, the invention offers, inter alia:

a fragment including a segment of 53 amino acids, called G1, and which corresponds to positions 665–717 of the CAEV Env protein;

a fragment including a segment of 82 amino acids, called G2, and which corresponds to positions 670–751 of the said Env protein;

a fragment including a segment of 38 amino acids, called G3, and which corresponds to positions 661–698 of the said Env protein;

a fragment including a segment of 52 amino acids, called G4, and which corresponds to positions 732–783 of the Env protein;

a fragment including a segment of 56 amino acids, called G5, and which corresponds to positions 694–749 of the said Env protein;

a fragment including a segment of 15 amino acids, called TM1, and which corresponds to positions 680–694 of the sequence of the CAEV Env protein and whose formula is:

Asp-Val-Leu-Glu-Ala-Thr-Tyr-Ala-Met-Val-Gln-His-Val-Ala-Lys (SEQ ID No. 8);

a fragment including a segment of 12 amino acids, called TM2, and which corresponds to positions 707–718 of the sequence of the CAEV Env protein and whose formula is:

Glu-Ala-Ile-Thr-Asp-Arg-Ile-Met-Leu-Tyr-Gln-Glu (SEQ ID No. 9);

a fragment including a segment of 15 amino acids, called TM3, and which corresponds to positions 717–731 of the said Env protein, which segment has the sequence:

Xaa-Glu-Leu-Asp-Cys-Trp-His-Tyr-Xaa-Xaa-Tyr-Cys-Xaa-Thr-Ser (SEQ ID No. 10), in which the amino acid Xaa in position 1, 9 and 10 represents His or Gln, the amino acid Xaa in position 13 represents Ile or Val; preferably, when the amino acid Xaa in position 9 represents His, the amino acid Xaa in position 10 and the amino acid Xaa in position 1 represents Gln and the amino acid Xaa in position 13 represents Ile and when the amino acid Xaa in position 9 represents Gln, the amino acid Xaa in position 10 and the amino acid Xaa in position 1 represent His and the amino acid Xaa in position 13 represents Val;

a fragment including a segment of 14 amino acids, called TM4, and which corresponds to positions 749–762 of the said Env protein, which segment has the sequence:

Cys-Thr-Trp-Gln-Gln-Trp-Glu-Arg-Glu-Le-Gln-Gly-Try-Asp (SEQ ID No. 11).

Unexpectedly, the set of sequences defined above allow specific and sensitive screening for a CAEV infection.

Also unexpectedly, among these fragments, the peptide fragments G5 or TM3 and G4 or TM4 exhibit a significantly high correlation with the development of the disease and therefore serve as particularly specific markers for the diagnosis of the CAEV infection; the peptide fragments G5 or TM3 also serve as markers for the diagnosis of the VISNA infection.

For the purposes of the present invention, the term peptide fragment corresponds to all the fragments including a segment of peptides as defined above, as well as the homologous peptides; in general, homologous peptides is understood to mean the peptide fragments whose position and function are equivalent, in CAEV (same location as that defined above, on the CAEV genome).

The set of the said peptides can advantageously id be obtained either by cloning or by synthesis, especially by Merrifield synthesis.

The subject of the present invention is also anti-CAEV antibodies, characterized in that they consist of antibodies specific for at least one peptide fragment derived from the transmembrane region of the CAEV Env protein, in accordance with the invention.

The subject of the present invention is also a process for the screening for a CAEV and/or the VISNA infection, characterized in that it consists in detecting the antibodies, optionally present in the biological sample, with the aid of at least one peptide or fragment of peptides in accordance with the invention, optionally attached to an appropriate solid support, by bringing the said biological sample into contact with the said peptide(s) or fragment(s) of peptides, to which the antibodies bind, if such antibodies are present in the sample to be analyzed, the reading of the result being visualized by an appropriate means, especially EIA, RIA, fluorescence.

According to an advantageous embodiment of the said process, the peptide is chosen from TM3 and TM4 or a mixture thereof.

The subject of the invention is also a process for the screening for a CAEV infection, characterized in that a biological sample, suitably treated to extract the DNA and/or the CAEV transcription products:

(1) is brought into contact with at least one nucleotide fragment as defined above, (2) after which, the hybrid formed is detected.

Advantageously, prior to step (1), the said DNA may be amplified.

The subject of the present invention is also a process for the screening for a CAEV infection, characterized in that it consists in detecting the CAEV envelope glycoproteins, by bringing a biological sample to be tested into contact with at least one anti-peptide antibody in accordance with the invention, the reading of the result being visualized by an appropriate means.

DESCRIPTION OF THE PREFERRED EMBODIMENTS

In addition to the preceding features, the invention also comprises other features which will emerge from the following description which refers to exemplary embodiments of the process which is the subject of the present invention.

It will be understood, however, that these examples are given solely by way of illustration of the object of the invention and do not constitute in any manner a limitation thereto.

EXAMPLE 1

Peptides in Accordance with the Invention

1) Construction of an Expression Library for the Peptides in Accordance with the Invention:

a) Cloning of the env Gene:

The env gene is obtained from an infectious clone of CAEV-CO (M. SALTARELLI et al., Virology, 1990, 179, 347–364).

The nucleotide and amino acid positions which define the various abovementioned env regions, correspond to the positions of the sequences as published in this reference.

The CAEV-CO clone consists of two plasmids, one containing a large portion of the CAEV-CO genome from the 5'-LTR and the second containing a short insert of 321 bp, comprising the sequences encoding the C-terminal portion of Env and the 3' portion of the viral LTR.

Figure 1:
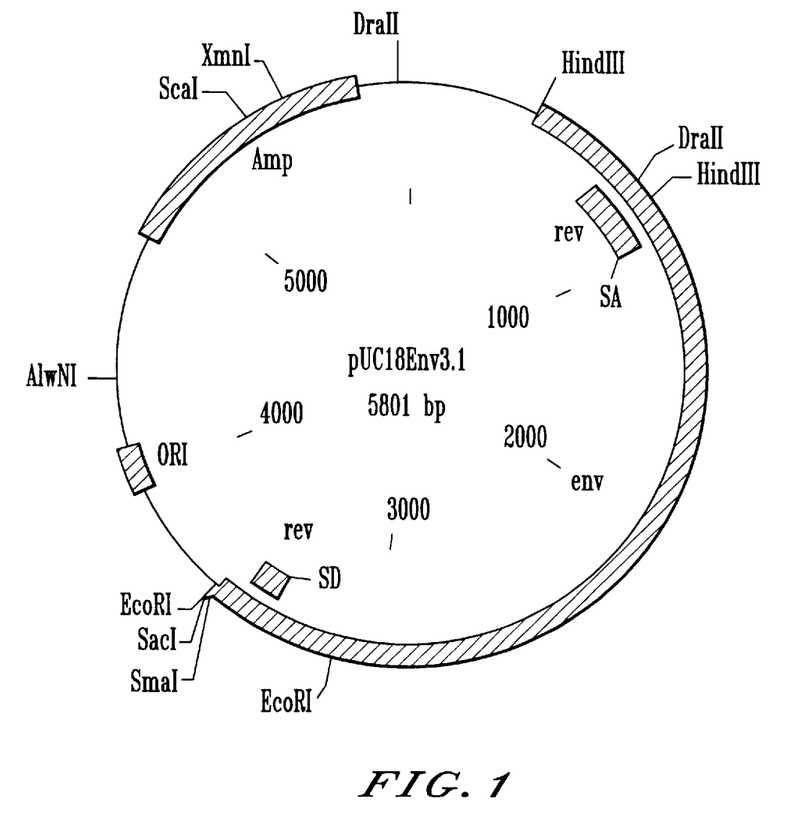
FIG. 1 is an illustration of pUC18Env3.1.

To generate a plasmid containing the region encoding the whole Env protein, the CAEV-CO SmaI-HindIII fragment is sharp cloned into the plasmid pUC18, as well as the HindIII-HindIII fragment of 321 bp; a construct called pUC18 env 3.1. is obtained (FIG. 1).

b) Construction of the λgt11 Expression Library:

The plasmid pUC18 env 3.1 is subjected to partial digestion with DNAase I at 15° C. (15 pg/ml of DNAase I in Tris-HCl, pH 7.4 in the presence of 1.5 mM $MgCl_2$, for 20 min), so as to obtain various DNA fragments, of about 200 bp.

These various fragments are treated with the Klenow fragment of DNAase polymerase of E. coli, so as to obtain blunt ends, for an efficient ligation with EcoRI binding sequences of 10 base pairs (bp) (Pharmacia).

The labelling of the DNA fragments with phosphorus-32 allows control of the subsequent stages.

The ligation products are then digested with the restriction enzyme EcoRI and separated by electrophoresis on 2% agarose gels LMP NUSIEVE (low melting temperature agarose), so as to select a set of fragments comprising between 100 and 200 bp and to remove the free binding sequences.

The selected fragments are extracted with phenol from the agarose; the various fragments obtained are then inserted into the EcoRI site of the phage λgt11.

The ligation products (recombinant phages) are then packaged in vitro. A library of $3.10^6$ phages is thus constituted.

An expression library is thus obtained for CAEV Env peptides, fused with β-galactosidase, and expressed in E. coli, using the vector λgt11.

A sample of the λgt11 library is inoculated on the E. coli Y1090 strain at a dilution representing $10^4$ phages per dish 90 cm in diameter.

The induction of the expression of the protein under the control of the Lac promoter is triggered at 42° C., in the presence of isopropyl-thio-β-galactosidase (IPTG). The recombinant phages are selected by the absence of a blue coloration of the lysis plagues.

c) Control of the Peptides Obtained:

The recombinant λgt11 phages allow the expression of the fragments of env genes under the control of the Lac promoter, after fusion of the env DNA with the E. coli β-galactosidase gene.

To control the quality of the said library, and also to obtain a higher titre 40 plaques were isolated and analyzed by PCR, using complementary λgt11 primers specific for the β-galactosidase portion of the λgt11 template as follows:

a total of 10 μl of phage lysate is diluted in 60 μl of water and heated at boiling temperature for 10 min. After microcentrifugation, 15 μl of supernatant are added to 85 μl of a PCR mixture containing 50 pM of each primer, 10 nM of each deoxynucleoside triphosphate and 0.5 U of Taq polymerase (Perkin-Elmer-Cetus), in a solution of 10 mM Tris-HCl, 50 mM KCl and 2 mM $MgCl_2$.

The λgt11 primers used are, as specified above, complementary to the β-galactosidase portion of the λgt11 template, namely:

5'GGTGGCGACGACTCCTGGACCCCG 3' (with sense primer) (SEQ ID No. 12)

5'TTGACACCAGACCAACTGGTAATG 3' (with antisense primer) (SEQ ID No 13).

The PCR comprises 32 cycles (cycle 1: 94° C., 2 min; cycles 2 to 31: 94° C., 15 sec/55° C., 30 sec/72° C., 30 sec; cycle 32: 72° C., 3 min).

The amplification products show that inserts of various sizes, comprising between 130 and 250 bp, are obtained.

These PCR-amplified fragments are then hybridized with three NcoI fragments radioactively labelled with phosphorus-32, representing the whole CAEV-CO Env sequence (probe 1: 6071–6456, probe 2: 6457–8071, probe 3: 8072–8712), indicating that the library is representative of the whole env gene.

2) Screening of the Library:

The λgt11 env library is screened using sera from 3 naturally infected goats, and having a high CAEV Gag protein titre, by the ELISA test.

The E. coli Y1090 probe is infected with $3 \times 10^4$ PFU of the original non-amplified library spread on plates and incubated at 42° C. for 4 hours.

The plates are then covered with nitrocellulose filters, saturated with 10 mM IPTG and incubated for 3 hours at 37°

C. so as to induce the expression of the fusion protein, β-galactosidase-Env peptide.

The filters are treated for an immunological screening with sera from 3 goats by separate incubation (2 filters per serum), using standard methods, such as the defatted milk-based procedure.

This screening makes it possible to isolate 5 strongly immunoreactive clones, which are sequenced according to the following procedure:

the PCR products are, separated on a 1.8% agarose gel and purified with the aid of QUIAEX beads (silica gel particles) (Qiagen), according to the manufacturer's instructions.

A total of 1 µl of dimethyl sulphoxide (DMSO) and 20 pM either of sense primers or of anti-sense primers, are added in a final volume of 10 µl.

This mixture is denatured at 100° C., for 12 min, and immediately transferred to a methanol ice bath.

1 µl of dithiothreitol (0.1M), 0.2 µl of dGTP (UBS), 0.5 µl of [$^{35}$S]ATP (600 Ci/mM), 0.6 µl of DMSO, 3.8 µl of dH$_2$O and 0.2 µl of Sequenase (UBS) are added.

The samples are incubated at room temperature for 1 min, and then for 15 min at 37° C.

The sequences of these 5 inserts, namely:

| Name of fragment | Position on the nucleic acid sequence | Positions on the Env protein |
| --- | --- | --- |
| G1 | 8003–8163 | 665–717 |
| G2 | 8019–8264 | 670–751 |
| G3 | 7991–8107 | 661–698 |
| G4 | 8204–8360 | 732–783 |
| G5 | 8090–8259 | 694–749 | are contained in the extracellular region of TM.

These results indicate the immunodominance and the conservation of these domains between the various viral isolates.

3) Map of the TM Imunodominant Epitopes in Accordance with the Invention:

a) Procedure:

A PEPSCAN (an Enzyme Linked Immunosorbent Assay) analysis is carried out so as to define precisely the immunoreactive TM epitopes.

Overlapping decapeptides covering the sequences between positions 8022 and 8327 of the CAEV Env protein were synthesized.

An immunoenzymatic test was carried out in accordance with the manufacturer's instructions (Cambridge Research Biochemicals), using sera obtained from 7 goats (1:100 dilution).

5 sera are obtained from goats naturally infected with CAEV strains, one serum is obtained from a goat experimentally infected with CAEV-CO, and one serum corresponds to a pool of 4 sera obtained from goats experimentally infected with the caprine arthritis encephalitis virus-CO.

Figure 2A:
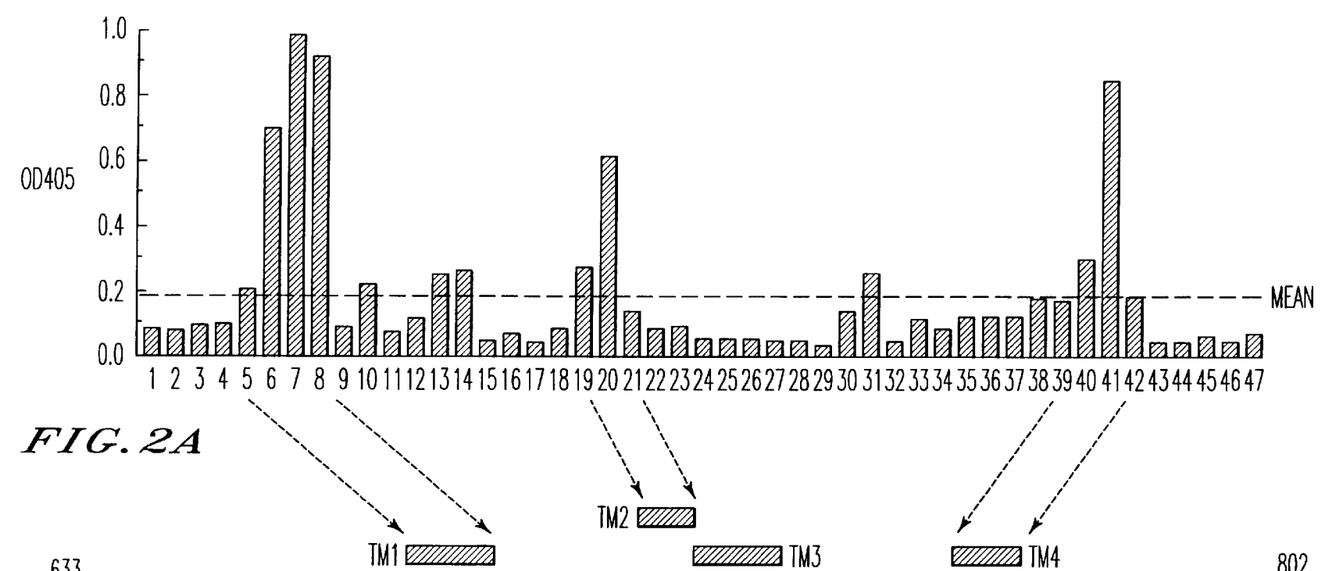
FIG. 2A illustrates the identification of three TM epitopes.
Figure 2B:
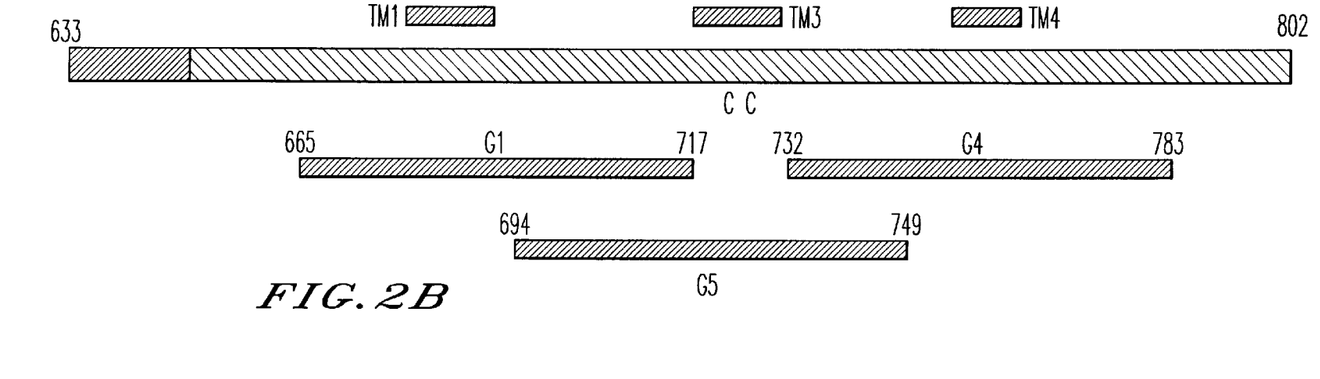
FIG. 2B shows the position of these three TM epitopes in the TM protein.

The reaction is detected by incubation in the presence of anti-goat rabbit Ig conjugated with peroxidase (Sigma), diluted 1:20,000 or in the presence of monoclonal antibodies conjugated with peroxidase (Chekit®) diluted 1:200, followed by visualization with the aid of 2,2'-azinaobis (3-ethylbenzthiazoline-6-sulphonic acid (ABTS, Sigma).

b) Results:

TM1, TM2 and TM4:

It is evident from these tests that 3 groups of overlapping peptides are reactive and define three different epitopes in accordance with FIG. 2, which IS comprises, on the x-axis, the various overlapping fragments studied and, on the y-axis, the optical density at 405 nm (FIG. 2A) as well as the position of the immunoreactive peptides on the sequence (FIG. 2B).

These peptides correspond to TM1, TM2 and TM4.

TM3:

Surprisingly, the region containing the two conserved cysteines, which is known to form an immunodominant and conserved structure in various lentiviruses does not react with the sera tested, but the peptide TM3, comprising this region, was nevertheless synthesized.

Another peptide, with the same sequence but chemically cyclized by a covalent bond between the two cysteines was also prepared (TM3c) so as to reproduce a loop structure which is considered to necessarily exist in the native TM protein.

A pool of sera obtained from 30 goats is tested by ELISA for its reactivity to TM3 and to TM3c.

All the sera recognize the two peptides; there is therefore no significant difference between TM3 and TM3C, such that the other experiments were carried out only with TM3c.

Figure 3A:
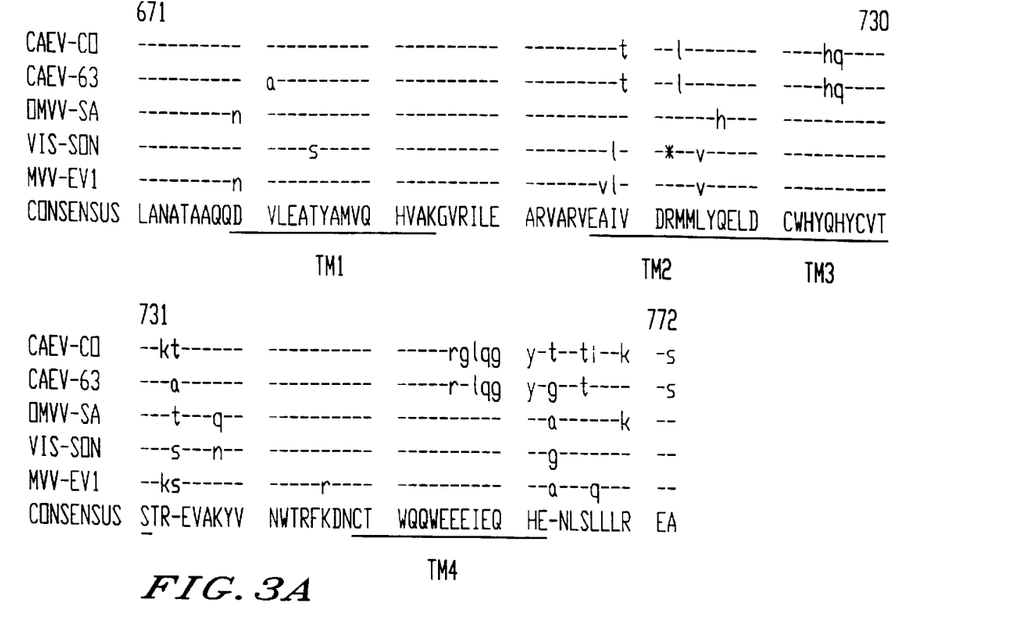
FIG. 3A (SEQ ID NO: 14–19) and FIG. 3B show a comparison of a portion of the Env proteins of a number of viruses.

The TM3 epitope is located in the most conserved env region, whereas the sequences corresponding to TM1, TM2 and TM4 exhibit variations (FIG. 3A) (SEQ ID NO: 14–19).

Figure 3B:
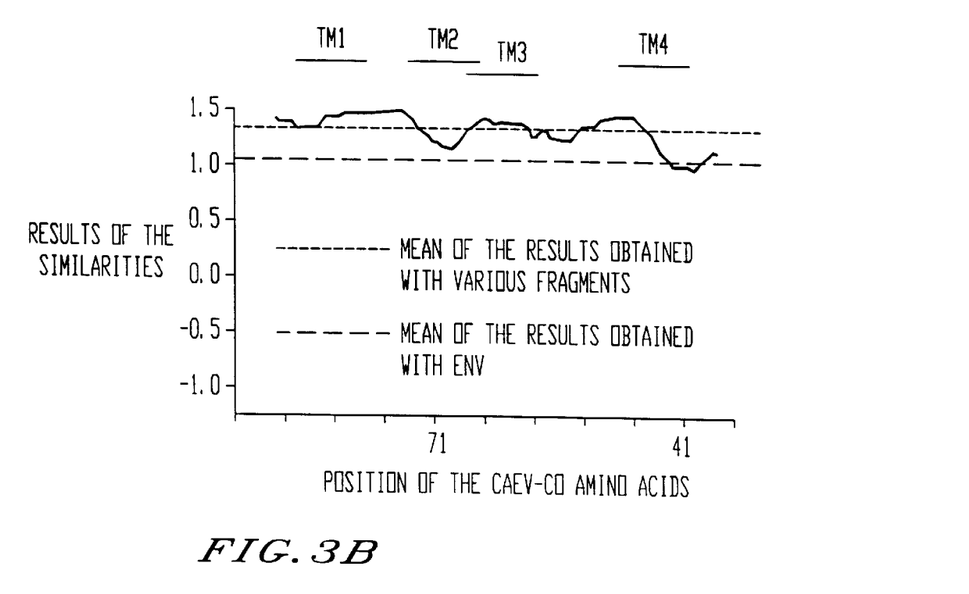
Figure 4A:
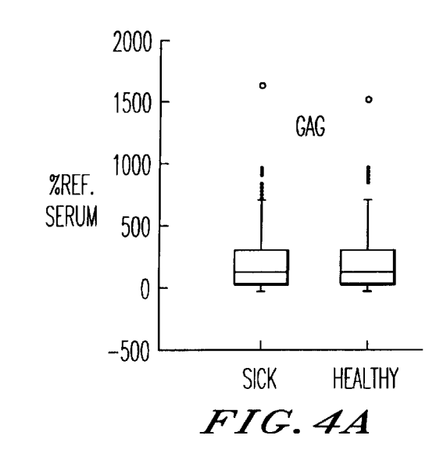
FIG. 4 illustrates the results of a test for screening for CAEV infection.
Figure 4B:
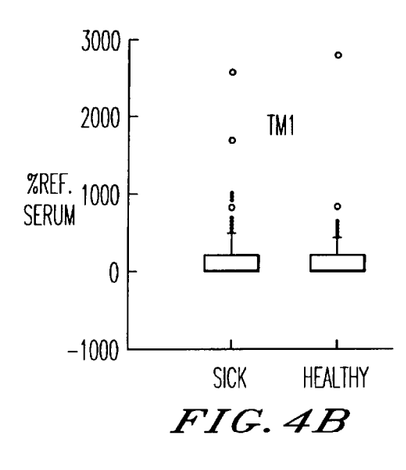
Figure 4C:
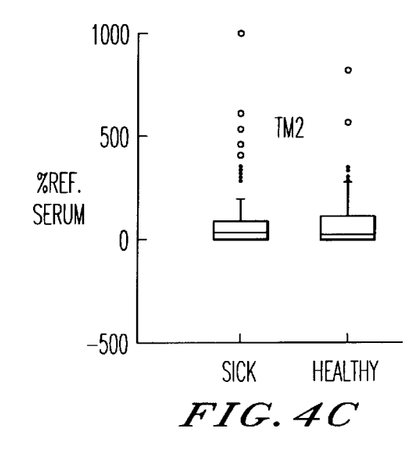
Figure 4D:
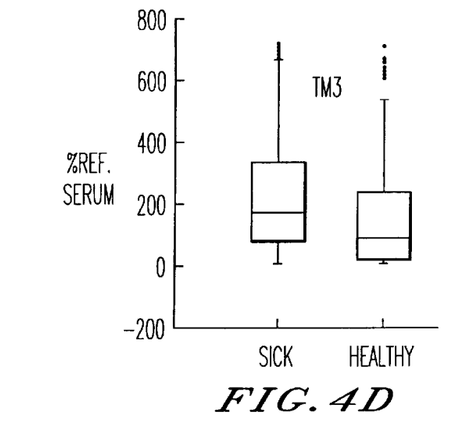
Figure 4E:
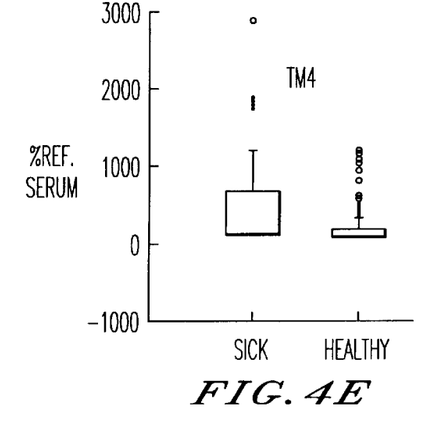

The comparative study and the alignment of the immunodominant TM sequences with 3 very similar MAEDI-VISNA molecular clones show a very strong similarity of the TM3 region relative to that of the whole Env protein (FIG. 3B).

Furthermore, a good correlation exists between the percentage similarity and the serological reactivity of the 4 peptides. In fact, the highest reactivity of the TM3 peptide, which is contained in the G5 fusion protein, confirms that this epitope is located in a highly conserved region, as is the case in the corresponding epitopes, of other lentiviruses.

TM4 also corresponds to a conserved region. Conversely, the G1 domain, which contains the TM1 and TM2 epitopes, appears to be more variable.

EXAMPLE 2

Test for Screening for a CAEV Infection

I—Immunoblot Analysis a) Procedure:

The domains binding to the antibodies, namely; G1: 8003–8163, G4: 8204–8360 and G5: 8090–8259 were expressed in the form of fusion proteins with β-galactosidase in the lysogenic E. coli bacteria Y1089, as specified above.

The lysates of bacteria containing the fusion proteins were prepared from a lysogenic-HPTG culture.

The lysates (40 µg/well) are separated on 10% SDS-PAGE (sodium dodecyl sulphate-polyacrylamide) gels and transferred onto nitrocellulose filters.

The non-specific sites are blocked by incubation with 3% defatted milk in a Tris-HCl buffer (10 mM) containing NaCl (1250 mM) and Tween 20 (0.1%).

The nitrocellulose bands are incubated with a goat serum diluted 1:100/1:800 overnight at 4° C.

The binding with the antibody is visualized by incubation with G protein conjugated with peroxidase, diluted 1:5000, followed by visualization with 4-chloro-1-naphtol (Sigma).

One lysate of bacteria infected with a non-recombinant phage λgt11 is used as negative control.

The sera collected before the experimental infection and a pool of sera obtained from non-infected goats are used as control for the antibodies.

Furthermore, the co-location of the immuno-reactive bands with the fusion proteins is checked with a monoclonal antibody directed against β-galactosidase (Promega); western blotting on the purified viral antigen is performed as specified in R. ZANONI et al., J. Clin. Microbiol., 1989, 27, 580–582.

b) Results:

The peptides G1, G4 and G5 as defined in Example 1, covering the immunoreactive region of the TM transmembrane protein are used in a Western blot to screen 60 sera from naturally infected goats from various herds, under the conditions above.

Table I below shows that the sera react with G5 and G4 at more than 95%, whereas only 60% react with G1.

TABLE I

SUMMARY OF THE 60 SERA TESTED

| TM Region | G1 | G4 | G5 |
|---|---|---|---|
| Positive sera | 39 | 57 | 57 |
| % of positive sera | 65% | 95% | 95% |

II—ELISA Method:

a) Procedure:

The peptides (TM1–TM4) were synthesized and purified. The TM3 and TM4 peptides were adsorbed on a microtiter plate as follows:

100 μl of a solution at 5 μg/ml in 0.1M sodium carbonate, pH 9.6 were adsorbed in each well of a microtiter plate (Nunc, MAXISORP microtiter plate), overnight at 4° C.

The TM1 peptide shows a weak binding and the TM2 peptide does not bind at all to these plates or to other ELISA plates tested.

For this reason, plates which allow covalent binding of derivatized peptides (Nunc Covalink®) were used for TM1 and TM2.

The derivatization and the adsorption of these peptides onto plates are carried out as described in J. SONDERGARD-ANDERSON et al., J. Immunol. Methods, 1990, 131, 99–104.

These peptides are solubilized in water (TM1: 1 mg/ml, TM2; 0.5 mg/ml).

An equal volume of freshly prepared aqueous solution of 0.1M N-hydroxysuccinimide (NHS, Sigma H-7377) and 1-ethyl-3-(3-dimethylaminopropyl)carbodiimide, HCl (EDC, Sigma E-6383) are added to a volume of peptide solution.

After 30 min at room temperature, the activated peptides are diluted in ice cold 0.1M carbonate buffer (pH 8.9) at 10 μg/ml and 100 μl/well are adsorbed by Covalink® plates overnight at 4° C.

The ELISA test is carried out as follows:

after coating the microtiter plates, they are washed three times with PES, the residual adsorption sites on the plates are saturated by incubating with 100 μl of PBS containing milk (1%) and Tween 20 (0.1%) (ELISA EB buffer) for 2 hours at room temperature.

After washing, 50 μl of goat serum, diluted 1:10, in EB buffer, are incubated for 2 and a half hours at room temperature.

After washing 4 times with EB buffer, peroxidase-conjugated G protein (diluted 1:5000 in PBS-Tween 20 0.1%) is added for 2 hours at room temperature.

After 5 washes with PBS, the adsorbed peroxidase-conjugate is visualized with ABTS, 0.2 mg/ml in acetic acid at 0.6%, pH 4.7 and at a final $H_2O_2$ concentration w/v of 0.01%.

b) Results:

The optical density is measured at 405 nm on tests carried out in duplicate. The results are normalized using, as standard, a set of goat sera, calibrated in a Gag-GST ELISA, carried out as described in R. G. ZANONI et al., J. Clin. Microbiol., 1991, 29, 1290–1294.

It is considered that there is a positive reaction when there is a reactivity greater than 25% of the reference serum.

190 sera from goats infected with the caprine arthritis-encephalitis virus, at a well-defined clinical stage, were tested according to the ELISA procedure for the reactivity with the 4 epitopes and with the Gag protein.

As illustrated in Table II below, most of the sera react with the TM3 peptide and with the Gag protein.

TABLE II

SUMMARY OF THE 190 SERA TESTED

| Peptide | TM1 | TM2 | TM3 | TM4 | gag |
|---|---|---|---|---|---|
| Positive sera* | 122 | 136 | 174 | 145 | 175 |
| % of positive sera | 64% | 72% | 92% | 76% | 93% |

*Reactivity greater than 25% of the reference serum

The peptides TM4, TM2 and TM1 react with most of the sera, although with lower percentages than for TM3.

Some sera, although reactive in Western blotting with a virus pellet as antigens, are negative in ELISA.

c) Statistical Analysis:

The optical density values obtained in ELISA were normalized and expressed as percentage reactivity, compared with a reference serum consisting, as specified above, of a set of sera seropositive towards CAEV.

The ELISA reactivities of the sera from animals in good health and from arthritic animals were compared.

A reactivity index (RI) is calculated for each serum tested and corresponds to:

$$RI = \frac{\% \text{ reactivity towards the } TM \text{ peptides}}{\% \text{ reactivity towards Gag protein}}$$

These results are illustrated in Table III below:

TABLE III

| | GAG | | TM1 | | TM2 | | TM3 | | TM4 | |
|---|---|---|---|---|---|---|---|---|---|---|
| Clinical status | Healthy | Ill | Healthy | Ill | Healthy | Ill | Healthy | Ill | Healthy | Ill |
| % of average reactivity | 268 | 249 | 148 | 189 | 73 | 92 | 147 | 205 | 143 | 317 |
| % of median reactivity | 179 | 154 | 14 | 80 | 22 | 34 | 77 | 160 | 7 | 125 |

TABLE III-continued

| | Peptide | | | | | | | | | |
|---|---|---|---|---|---|---|---|---|---|---|
| | GAG | | TM1 | | TM2 | | TM3 | | TM4 | |
| Clinical status | Healthy | Ill | Healthy | Ill | Healthy | Ill | Healthy | Ill | Healthy | Ill |
| Reactivity index | 1 | 1 | 1.57 | 2.14 | 0.67 | 0.86 | 1.79 | 2.51 | 2.6 | 3.4 |

The sera from arthritic goats show a high reactivity with TM1, TM3 and more specifically with TM4, compared with the sera from animals in good health (TM1: U=5328.0, p=0.014, TM3: U=11468.0, p−0.002; TM4: U−5964.5, p<0.001).

On the other hand, there is no significant difference between the two groups of animals as regards the reactivity of the sera towards Gag and towards TM2 (Gag: U=4106.0, p−0.391; TM2: U=4905.5, p−0.198).

These results are illustrated in FIG. 4.

Comparison of the reactivity of the sera from goats in good health and from arthritic goats with the 4 TM peptides and the Gag protein revealed the existence of a correlation between the development of viral arthritis and the reactivity towards the TM1, TM3 and TM4 epitopes. This correlation was not found for the anti-Gag reactivity.

The screening for the presence of the abovementioned TM fragments (or of the anti-TM antibodies) has a predictive value, with the aim of evaluating the appearance of the clinical disease and makes it possible to take the measures necessary for a better protection of the herds.

III—Interpretation of the Results Obtained in I and in II.

a) Sensitivity of the Tests:

There is some difference between the Western blot results as regards the G4 peptide and the ELISA results obtained with TM4.

The Western blot is found to be more sensitive for this epitope, no doubt because this peptide fused with β-galactosidase has a conformation which is not present in the free peptide or because it contains more than one epitope.

About 35% of the animals do not react with the TM1 and TM2 epitopes in both tests.

b) Benefit and Properties of the Peptides Selected.

The results obtained made it possible to identify the determinants involved in the correlation serological reactivity-development of the viral arthritis, and therefore allow a better monitoring of this disease.

Interestingly, the TM3 epitope of the CAEV TM protein has the same location as the immunodominant epitope of other lentiviruses such as the lentiviruses which cause an immuno deficiency: HIV, SIV and FIV.

This epitope is located in a region containing a structure defined by two cysteines which is conserved by all lentiviruses in spite of the absence of a primary sequence homology.

In HIV-1, SIV and FIV, the sequence between the cysteines is highly conserved between the various viral isolates of the same species.

This reflects a high selective pressure for conservation, probably dictated by structural constraints.

Unexpectedly, it appeared that the reactivity of TM3 and TM4 towards antibodies produced during a CAEV infection exhibits a significantly high correlation with the development of the disease.

If the conserved and immunogenic regions of TM do not mutate, because of functional constraints, the continuous appearance of new env variants causes a permanent stimulation of the immune system, which perpetuates and amplifies the production of antibodies against the constant TM epitopes.

Consequently, the selected peptides are of particular benefit in the screening for and study of the humeral response to these conserved epitopes and in the study of the monitoring and of the development of caprine arthritis.

EXAMPLE 3

Test for Screening for a VISNA Infection

An assay was carried out to test the reactivity of the TM3 and TM4 peptides with sera from sheep infected with the VISNA virus. 40 sera obtained from breeding sheep were tested with the peptides in accordance with the invention ("ELISA peptides" method) and were compared with the precipitate CHEKIT (CAEV/MVV enzyme immunoassay kit) test.

The results are summarized in Table IV below:

TABLE IV

| number of sera in category | 10 | 8 | 9 | 12 | 1 |
|---|---|---|---|---|---|
| CHEKIT (CAEV/MVV enzyme immunoassay kit) | + | + | + | − | − |
| TM3 | + | + | − | − | + |
| TM4 | + | − | − | − | + |

It appears that the ELISA TM3 is more sensitive than ELISA TM4. 18 sera were reacted with TM3 and with the CHEKIT (CAEV/MVV enzyme immunoassay kit) test and 12 sera are negative with the three tests. 10 sera gave contradictory results between the CHEKIT (CAEV/MVV immunoassay kit) test and the TM3 test: 9 are positive by the CHEKIT (CAEV/MVV immunoassay kit) test and negative with the peptides, 1 gives the opposite results.

6 of the sera positive with the CHEKIT (CAEV/MVV immunoassay kit) test and negative with TM3 were able to be controlled by immunoblotting: 5 out of 6 were negative.

It therefore appears that a large number of false-positive reactions are detected with the CHEKIT (CAEV/MVV enzyme immunoassay kit) test and that the ELISA TM3 in accordance with the invention is significantly more specific. The only case of a serum reactive with TM3 and TM4 and negative with the CHEKIT (CAEV/MVV enzyme immunoassay kit) test requires additional tools to determine if it is a true- or a false-positive reaction.

As evident from the above, the invention is not in the least limited to its embodiments, modes of implementation and application would have just been described more explicitly; it embraces on the contrary all the variants which may occur to a specialist in this field, without departing from the framework or the scope of the present invention.

We claim:

1. A nucleic acid fragment encoding a peptide fragment, wherein the peptide fragment contains at least one immunodominant epitope of the transmembrane region of the CAEV Env protein;
wherein the nucleic acid fragment comprises a sequence selected from the group consisting of SEQ ID NO:1, the sequence corresponding to positions 8019–8264 of the gene encoding the CAEV Env protein, the sequence corresponding to positions 7991–8107 of the gene encoding the CAEV Env protein, SEQ ID NO:2, SEQ ID NO:3, SEQ ID NO:4, SEQ ID NO:6, and SEQ ID NO:7;
wherein SEQ ID NO:1 encodes the G1 peptide fragment, the sequence corresponding to positions 8019–8264 encodes the G2 peptide fragment, the sequence corresponding to positions 7991–8107 encodes the G3 peptide fragment, SEQ ID NO:2 encodes the G4 peptide fragment, SEQ ID NO:3 encodes the G5 peptide fragment, SEQ ID NO:4 encodes the TM1 peptide fragment, SEQ ID NO:6 encodes the TM3 peptide fragment, and SEQ ID NO:7 encodes the TM4 peptide fragment.

2. A peptide fragment,
wherein the peptide fragment contains at least one immunodominant epitope of the transmembrane region of the CAEV Env protein;
wherein the peptide fragment comprises a sequence selected from the group consisting of the sequence corresponding to positions 665–717 of the CAEV Env protein, the sequence corresponding to positions 670–751 of the CAEV Env protein, the sequence corresponding to positions 661–698 of the CAEV Env protein, the sequence corresponding to positions 732–783 of the CAEV Env protein, the sequence corresponding to positions 694–749 of the CAEV Env protein, the sequence corresponding to positions 680–694 of the CAEV Env protein, SEQ ID NO:8, SEQ ID NO:10, and SEQ ID NO: 11,
wherein positions 1, 9, and 10 of SEQ ID NO:10 are each His or Gln, and position 13 of SEQ ID NO:10 is Ile or Val,
wherein the sequence corresponding to positions 665–717 comprises the G1 peptide fragment, the sequence corresponding to positions 670–751 comprises the G2 peptide fragment, the sequence corresponding to positions 661–698 comprises the G3 peptide fragment, the sequence corresponding to positions 732–783 comprises the G4 peptide fragment, the sequence corresponding to positions 694–749 comprises the G5 peptide fragment, the sequence corresponding to positions 680–694 comprises the TM1 peptide fragment, SEQ ID NO:8 comprises the TM3 peptide fragment, SEQ ID NO: 10 comprises the G1 peptide fragment, and SEQ ID NO:11 comprises the TM4 peptide fragment.

3. The peptide fragment of claim 2, wherein positions 1 and 10 of SEQ ID NO:10 are each Gln, position 9 of SEQ ID NO:10 is His, and position 13 of SEQ ID:NO 10 is Ile.

4. The peptide fragment of claim 2, wherein positions 1 and 10 of SEQ ID NO:10 are each His, position 9 of SEQ ID NO:10 is Gln, and position 13 of SEQ ID:NO 10 is Val.

5. A reagent for the screening of a CAEV infection, wherein the reagent comprises the nucleic acid fragment of claim 1.

6. A reagent for the screening of a CAEV infection, wherein the reagent comprises the peptide fragment of claim 2.

7. An anti-CAEV antibody specific to the peptide fragment of claim 2.

8. A method for detecting a CAEV infection or a VISNA infection in a patient comprising:
(a) contacting a biological sample from the patient with the peptide fragment of claim 2; and
(b) determining if an immunological complex comprising the peptide fragment and an antibody is formed, thereby detecting the CAEV infection or the VISNA infection in the patient if the immunological complex is formed.

9. The method of claim 8, wherein the peptide fragment in step (a) is bound to a solid support.

10. The method of claim 8, wherein step (b) is conducted using EIA, RIA, and fluorescence.

11. The method of claim 8, wherein the peptide fragment is selected from the group consisting of the TM3 peptide fragment, the TM4 peptide fragment, or a mixture thereof.

12. A method for detecting a CAEV infection in a patient comprising:
(a) obtaining a biological sample from the patient;

(b) extracting a nucleic acid from the sample;

(c) contacting the nucleic acid from the sample with the nucleic acid fragment of claim 1; and (d) determining if a hybrid comprising a strand of the nucleic acid from the sample and a strand from the nucleic acid fragment of claim 1 is formed, thereby detecting the CAEV infection in the patient if the hybrid is formed.

13. The method of claim 12, further comprising, in between step (c) and step (d), amplifying the nucleic acid from the sample.

14. A method for detecting a CAEV infection in a patient comprising:

(a) contacting a biological sample from the patient with the anti-CAEV antibody of claim 7, and (b) determining if an immunological complex comprising the antibody and a CAEV Env protein is formed, thereby detecting the CAEV infection in the patient if the immunological complex is formed.

15. The method of claim 14, wherein step (b) is conducted using EIA, RIA, and fluorescence.

\* \* \* \* \*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 161 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
TAAGGCAGCT  GTCCAGACCC  TTGCTAATGC  AACTGCTGCA  CAGCAGGATG  TGTTAGAGGC      60
AACCTATGCC  ATGGTACAGC  ATGTGGCTAA  AGGCGTACGA  ATCTTGGAAG  CTCGAGTGGC     120
TCGAGTGGAA  GCTATCACAG  ATAGAATAAT  GCTATACCAA  G                         161
```

( 2 ) INFORMATION FOR SEQ ID NO:2:

( i ) SEQUENCE CHARACTERISTICS:
        ( A ) LENGTH: 157 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

```
TACAAAAACA  GAAGTAGCAA  AATATATCAA  TTGGACGAGG  TTTAAGGATA  ATTGCACATG      60
GCAGCAGTGG  GAGAGAGGAT  TACAGGGGTA  TGATACAAAC  TTAACAATAC  TGTTAAAGGA     120
ATCAGCAGCA  ATGACACAAC  TAGCAGAAGA  GCAAGCA                                157
```

( 2 ) INFORMATION FOR SEQ ID NO:3:

( i ) SEQUENCE CHARACTERISTICS:
        ( A ) LENGTH: 170 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

```
TAAAGGCGTA  CGAATCTTGG  AAGCTCGAGT  GGCTCGAGTG  GAAGCTATCA  CAGATAGAAT      60
AATGCTATAC  CAAGAATTGG  ATTGTTGGCA  CTATCATCAA  TACTGTATAA  CCTCTACAAA     120
AACAGAAGTA  GCAAAATATA  TCAATTGGAC  GAGGTTTAAG  GATAATTGCA                 170
```

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

```
GATGTGTTAG  AGGCAACCTA  TGCCATGGTA  CAGCATGTGG  CTAAA                       45
```

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

GAAGCTATCA CAGATAGAAT AATGCTATAC CAAGAA        36

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:6:

CAAGAATTGG ATTGTTGGCA CTATCATCAA TACTGTATAA CCTCT        45

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

TGCACATGGC AGCAGTGGGA GAGAGGATTA CAGGGGTATG AT        42

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:8:

Asp Val Leu Glu Ala Thr Tyr Ala Met Val Gln His Val Ala Lys
 1              5                    10                 15

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:9:

Glu Ala Ile Thr Asp Arg Ile Met Leu Tyr Gln Glu
 1              5                    10

( 2 ) INFORMATION FOR SEQ ID NO:10:

( i ) SEQUENCE CHARACTERISTICS:

(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Xaa Glu Leu Asp Cys Trp His Tyr Xaa Xaa Tyr Cys Xaa Thr Ser
1               5                   10                  15

(2) INFORMATION FOR SEQ ID NO:11:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Cys Thr Trp Gln Gln Trp Glu Arg Glu Leu Gln Gly Tyr Asp
1               5                   10

(2) INFORMATION FOR SEQ ID NO:12:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "SENSE PRIMER"

(xi) SEQUENCE DESCRIPTION: SEQ ID NO:12:

GGTGGCGACG ACTCCTGGAG CCCG                                           24

(2) INFORMATION FOR SEQ ID NO:13:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "ANTISENSE PRIMER"

(xi) SEQUENCE DESCRIPTION: SEQ ID NO:13:

TTGACACCAG ACCAACTGGT AATG                                           24

(2) INFORMATION FOR SEQ ID NO:14:

(i) SEQUENCE CHARACTERISTICS:
    (A) LENGTH: 102 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:14:

Leu Ala Asn Ala Thr Ala Ala Gln Gln Asp Val Leu Glu Ala Thr Tyr
1               5                   10                  15

Ala Met Val Gln His Val Ala Lys Gly Val Arg Ile Leu Glu Ala Arg
            20                  25                  30

Val Ala Arg Val Glu Ala Ile Thr Asp Arg Leu Met Leu Tyr Gln Glu

|   | 35 | | | | 40 | | | | 45 | | | |
|---|---|---|---|---|---|---|---|---|---|---|---|---|

Leu Asp Cys Trp His Tyr His Gln Tyr Cys Val Thr Ser Thr Lys Thr
     50                 55                60

Glu Val Ala Lys Tyr Val Asn Trp Thr Arg Phe Lys Asp Asn Cys Thr
 65                 70                75                80

Trp Gln Gln Trp Glu Arg Gly Leu Gln Gly Tyr Glu Thr Asn Leu Thr
                 85                90                95

Ile Leu Leu Lys Glu Ser
            100

( 2 ) INFORMATION FOR SEQ ID NO:15:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear    ( i i ) MOLECULE TYPE: protein    ( x i ) SEQUENCE DESCRIPTION: SEQ ID NO:15:

Leu Ala Asn Ala Thr Ala Ala Gln Gln Asp Ala Leu Glu Ala Thr Tyr
 1                5                  10                15

Ala Met Val Gln His Val Ala Lys Gly Val Arg Ile Leu Glu Ala Arg
               20                25                30

Val Ala Arg Val Glu Ala Ile Thr Asp Arg Ile Met Leu Tyr Gln Glu
         35                40              45

Leu Asp Cys Trp His Tyr His Gln Tyr Cys Val Thr Ser Thr Arg Ala
     50                55                60

Glu Val Ala Lys Tyr Val Asn Trp Thr Arg Phe Lys Asp Asn Cys Thr
 65                 70                75                80

Trp Gln Gln Trp Glu Arg Glu Leu Gln Gly Tyr Glu Gly Asn Leu Thr
               85                90                95

Leu Leu Leu Arg Glu Ser
            100

( 2 ) INFORMATION FOR SEQ ID NO:16:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear    ( i i ) MOLECULE TYPE: protein    ( x i ) SEQUENCE DESCRIPTION: SEQ ID NO:16:

Leu Ala Asn Ala Thr Ala Ala Gln Gln Asn Val Leu Glu Ala Thr Tyr
 1                5                  10                15

Ala Met Val Gln His Val Ala Lys Gly Val Arg Ile Leu Glu Ala Arg
               20                25                30

Val Ala Arg Val Glu Ala Ile Val Asp Arg Met Met Leu Tyr His Glu
         35                40              45

Leu Asp Cys Trp His Tyr Gln His Tyr Cys Val Thr Ser Thr Arg Thr
     50                55                60

Glu Val Ala Gln Tyr Val Asn Trp Thr Arg Phe Lys Asp Asn Cys Thr
 65                 70                75                80

Trp Gln Gln Trp Glu Glu Glu Ile Glu Gln His Glu Ala Asn Leu Ser
               85                90                95

Leu Leu Leu Lys Glu Ala

100

(2) INFORMATION FOR SEQ ID NO:17:

(i) SEQUENCE CHARACTERISTICS:
        (A) LENGTH: 102 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:17:

```
Leu Ala Asn Ala Thr Ala Ala Gln Gln Asp Val Leu Glu Ala Ser Tyr
 1               5                  10                  15
Ala Met Val Gln His Val Ala Lys Gly Val Arg Ile Leu Glu Ala Arg
                20                  25                  30
Val Ala Arg Val Glu Ala Leu Val Asp Arg Met Met Val Tyr Gln Glu
                35                  40                  45
Leu Asp Cys Trp His Tyr Gln His Tyr Cys Val Thr Ser Thr Arg Ser
                50                  55                  60
Glu Val Ala Asn Tyr Val Asn Trp Thr Arg Phe Lys Asp Asn Cys Thr
 65                  70                  75                  80
Trp Gln Gln Trp Glu Glu Glu Ile Glu Gln His Glu Gly Asn Leu Ser
                85                  90                  95
Leu Leu Leu Arg Glu Ala
                100
```

(2) INFORMATION FOR SEQ ID NO:18:

(i) SEQUENCE CHARACTERISTICS:
        (A) LENGTH: 102 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:18:

```
Leu Ala Asn Ala Thr Ala Ala Gln Gln Asn Val Leu Glu Ala Thr Tyr
 1               5                  10                  15
Ala Met Val Gln His Val Ala Lys Gly Val Arg Ile Leu Glu Ala Arg
                20                  25                  30
Val Ala Arg Val Glu Val Leu Val Asp Arg Met Met Val Tyr Gln Glu
                35                  40                  45
Leu Asp Cys Trp His Tyr Gln His Tyr Cys Val Thr Ser Thr Lys Ser
                50                  55                  60
Glu Val Ala Lys Tyr Val Asn Trp Thr Arg Phe Lys Asp Asn Cys Thr
 65                  70                  75                  80
Trp Gln Gln Trp Glu Glu Glu Ile Glu Gln His Glu Ala Asn Leu Ser
                85                  90                  95
Gln Leu Leu Arg Glu Ala
                100
```

(2) INFORMATION FOR SEQ ID NO:19:

(i) SEQUENCE CHARACTERISTICS:
        (A) LENGTH: 102 amino acids
        (B) TYPE: amino acid
        (C) STRANDEDNESS: single
        (D) TOPOLOGY: linear     (ii) MOLECULE TYPE: protein (xi) SEQUENCE DESCRIPTION: SEQ ID NO:19:

| Leu | Ala | Asn | Ala | Thr | Ala | Ala | Gln | Gln | Asp | Val | Leu | Glu | Ala | Thr | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Met | Val | Gln | His | Val | Ala | Lys | Gly | Val | Arg | Ile | Leu | Glu | Ala | Arg |
|     |     |     | 20  |     |     |     |     | 25  |     |     |     |     | 30  |     |     |
| Val | Ala | Arg | Val | Glu | Ala | Ile | Val | Asp | Arg | Met | Met | Leu | Tyr | Gln | Glu |
|     |     | 35  |     |     |     |     | 40  |     |     |     |     | 45  |     |     |     |
| Leu | Asp | Cys | Trp | His | Tyr | Gln | His | Tyr | Cys | Val | Thr | Ser | Thr | Arg | Xaa |
|     | 50  |     |     |     |     | 55  |     |     |     |     | 60  |     |     |     |     |
| Glu | Val | Ala | Lys | Tyr | Val | Asn | Trp | Thr | Arg | Phe | Lys | Asp | Asn | Cys | Thr |
| 65  |     |     |     |     | 70  |     |     |     |     | 75  |     |     |     |     | 80  |
| Trp | Gln | Gln | Trp | Glu | Glu | Glu | Ile | Glu | Gln | His | Glu | Xaa | Asn | Leu | Ser |
|     |     |     |     | 85  |     |     |     |     | 90  |     |     |     |     | 95  |     |
| Leu | Leu | Leu | Arg | Glu | Ala |     |     |     |     |     |     |     |     |     |     |
|     |     |     | 100 |     |     |     |     |     |     |     |     |     |     |     |     |